United States Patent [19]
Ito et al.

[11] Patent Number: 5,374,627
[45] Date of Patent: Dec. 20, 1994

[54] METHODS FOR PROTECTING VEGETABLES, TURFGRASS, RICE AND FRUIT TREES FROM FUNGI AND BACTERIA

[75] Inventors: Kazuhiro Ito; Etsuzo Entani, both of Handa; Yoshiya Kawamura, Kounan, all of Japan

[73] Assignee: Nakano Vinegar Co., Ltd., Handa, Japan

[21] Appl. No.: 6,145

[22] Filed: Jan. 19, 1993

Related U.S. Application Data

[63] Continuation of Ser. No. 754,535, Sep. 4, 1991, abandoned.

[30] Foreign Application Priority Data

Sep. 21, 1990 [JP] Japan .................................. 2-250244
Jul. 3, 1991 [JP] Japan .................................. 3-188233

[51] Int. Cl.$^5$ ...................... A01N 43/04; A01N 25/00
[52] U.S. Cl. ..................................... 514/55; 514/777; 504/100; 504/101
[58] Field of Search ................ 514/55, 777; 426/49, 426/52, 635, 655, 69; 47/57.6; 56/13.5; 504/100, 101

[56] References Cited

U.S. PATENT DOCUMENTS 3,975,546  8/1976  Stahmann .......................... 426/655
4,356,196 10/1982  Hultquist .......................... 426/635
4,554,155 11/1985  Allan et al. ........................ 514/777

FOREIGN PATENT DOCUMENTS 1128775  5/1989  Japan .

OTHER PUBLICATIONS

Brown et al; Developmental Industrial Microbiology; vol. (23); pp. 513–519; 1982.
Lewis et al; Crop Protection Journal; vol. (10), pp. 95–105; 1991.
Hirano et al; "Effects of Chitosam Pectic Acid, Lysozyme, and Chitanase on the Growth of Several Phytopathogens", Agricultural Biological Chemistry Journal; vol. (53) 11; pp. 3065–3066; May, 1989.
Kendra et al, "Characterization of the Smallest Chitosan Oligomer That Is Maximally Antifungal to *Fusarium solani* and Elicits Isatin Formation in *Pisum sativum*", 1984, pp. 276–281, Experimental Mycology 8.
Stossel et al, "Effect of Chitosan, Chitin and some Aminosugars on Growth of Various Soilborne Phytophathogenic Fungi", (1984), pp. 82–90, Phytopath.Z.
C. R. Allan et al, "The Fungicidal Effect on Fungi of Varying Cell Wall Composition", (1979), pp. 285–287, Experimental Mycology 3.

*Primary Examiner*—Jeffrey E. Russel
*Assistant Examiner*—Louise N. Leary
*Attorney, Agent, or Firm*—Frishauf, Holtz, Goodman & Woodward

[57] ABSTRACT

A variety of plant diseases and damage by certain pests in agricultural and horticultural plants can be efficiently controlled without substantial chemical injuries by applying a plant-protecting composition which comprises (a) 1 part by weight of a chitosan hydrolyzate having an average molecular weight of 10,000 to 50,000, obtained by acid hydrolysis or enzymatic hydrolysis of chitosan and (b) 0.25 to 4 parts by weight of acetic acid. Any possible chemical injury to plants caused by applying the composition can be further reduced when the composition is admixed with a deproteinized juice of alfalfa leaves.

18 Claims, No Drawings

METHODS FOR PROTECTING VEGETABLES, TURFGRASS, RICE AND FRUIT TREES FROM FUNGI AND BACTERIA

This application is a continuation of application Ser. No. 07/754,535, filed Sep. 4, 1991, now abandoned.

BACKGROUND OF THE INVENTION

The present invention relates to a novel agricultural chemical composition containing a hydrolyzate of chitosan and acetic acid useful for protecting various plants from harmful organisms or preventing plant diseases caused by harmful organisms as well as to a method for preventing plant diseases caused by harmful organisms by using the chemical composition.

As is known, chitosan is a deacetylation product of chitin contained in the crusts of various crustacean animals such as crabs and lobsters and cell walls of certain microorganisms. Chitosan can be hydrolyzed to give a low molecular weight chitosan which is referred to as a chitosan hydrolyzate hereinbelow.

It is known that chitosan and chitosan hydrolyzates have influences on the growth of various phytopathogenic fungi as reported in *Experimental Mycology*, volume 3, pages 285-287 (1979), Phytopathologische Zeitschrift, volume 111, pages 82-89 (1984), *Experimental Mycology*, volume 8, pages 276-281 (1984) and *Agricultural and Biological Chemistry*, volume 53, pages 3065-3066 (1989) and a proposal is made for the utilization thereof as an agricultural chemical agent for preventing black spot of pear in practice (see Japanese patent Kokai No. 62-198604).

The agricultural chemical agents containing chitosan or a chitosan hydrolyzate heretofore proposed have several problems that the effectiveness thereof is limited to several particular plant diseases and that damages to the plants caused by the chemicals is unavoidable when the agent is used in high concentrations. Accordingly, it is eagerly desired to develop an agricultural chemical agent having a broad anti-microbial spectrum to exhibit effectiveness against various plant diseases without limitation and capable of exhibiting the desired effect by using in a low concentration free from the problem of damage to plants due to the chemicals.

On the other hand, it is also known that acetic acid and other organic acids have a microbicidal action and these organic acids can be used as an active ingredient in microbicides utilizing the microbicidal action thereof. In the field of food industry in which the problem of chemical injury is of relatively low importance as compared with agriculture treating living plants, in particular, organic acids are under practical use as a microbicide or microbiostat.

In the microbicides and microbiostats containing an organic acid, however, it is essential to maintain a high concentration of the organic acid as the active ingredient while, when an agricultural chemical agent containing an organic acid in a concentration high enough to exhibit the microbicidal action is applied to a living plant, serious chemical injuries are caused in the plant so that applicability of such an agent to agriculture is questionable. Furthermore, it is impossible to directly apply acetic acid in a high concentration to exhibit the microbicidal action to plants having relatively low resistance against chemical injuries because acetic acid is one of the organic acids which exhibits particularly serious chemical injuries to plants.

As to the application of the supernatant liquor obtained by the deproteinization of green alfalfa leaves, which is referred to as a brown juice hereinbelow, to agricultural plants, on the other hand, an attempt has been made to utilize the same as a fertilizer although the attempt has not led to establishment of the technology. Moreover, absolutely nothing has been thought of the utilization of the brown juice as an agricultural chemical agent for protecting plants from harmful organisms.

Further, nothing has been taught concerning pest control by using chitosan or chitosan hydrolyzates and organic acids such as acetic acid.

SUMMARY OF THE INVENTION

The present invention accordingly has an object to provide a novel agricultural chemical composition containing a chitosan hydrolyzate free from the above described problems and disadvantages in the prior art agricultural chemical agents. The inventors have conducted extensive investigations to achieve the above object and arrived at a discovery that a composition comprising a chitosan hydrolyzate and acetic acid in a specific proportion with optional admixture of a brown juice can be effectively utilized as an agricultural chemical composition for protecting plants from harmful organisms leading to completion of the present invention.

Thus, the present invention provides a novel agricultural chemical composition which comprises 1 part by weight of a chitosan hydrolyzate and from 0.25 to 4 parts by weight of acetic acid with optional admixture of a brown juice. The invention also provides a method for protecting plants from harmful organisms by utilizing the above defined agricultural chemical composition, for example, against bacterial soft rot of vegetables, against spring deadspot, Rhizoctonia large patch, Helminthosporium leaf blight and Rhizoctonia brown patch of and vermin damage by lawn grass cutworm in turfgrasses, against bacterial grain rot of rice and against scab of fruit trees.

DETAILED DESCRIPTION OF THE PREFERRED EMBODIMENTS

The chitosan hydrolyzate as an essential ingredient in the inventive composition is obtained by decomposing chitosan as a deacetylation product of chitin by using an acid or an enzyme to such an extent that the decomposition product may have an appropriate molecular weight. The acid used in the acid decomposition of chitosan can be any of organic and inorganic acids including acetic acid, lactic acid, citric acid, malic acid and the like as the examples of organic acids and hydrochloric acid, sulfuric acid and the like as the examples of inorganic acids.

The enzyme used in the enzymatic decomposition of chitosan is exemplified by chitosanase, papain, cellulase, acidic protease, pectinase and the like.

The process of the acid decomposition of chitosan is disclosed in Japanese Patent Kokai No. 128775/1989 and elsewhere and the process of the enzymatic decomposition of chitosan is disclosed in Japanese Patent Kokai No. 291799/1989 and elsewhere. The chitosan hydrolyzate used in the invention is not particularly limitative relative to the method for the decomposition of chitosan. Preferably, the chitosan hydrolyzate should have an average molecular weight in the range from about 10,000 to about 50,000 in respect of the relatively high antimicrobial activity as is taught in Japanese Patent Kokai No. 128775/1989.

The acetic acid as the other essential ingredient in the inventive composition is not particularly limitative in connection with the origin including synthetic products of acetic acid, acetic acid-containing liquids, vinegars and the like. An example of the above mentioned acetic acid-containing liquid is the vinegar solution described in Japanese Patent Registration No. 959,222 which contains, besides acetic acid, salts of acetic acid and is advantageous in respect of the less serious chemical injuries to the plants than acetic acid per se.

Further, the brown juice as an optional ingredient in the inventive composition is obtained by removing proteins by heating alfalfa utilized as a food or feed to husbandry animals. A process for the preparation of a brown juice from alfalfa is described in Japanese Patent Kokai No. 58905/1991 and Japanese Patent Application No. 159929/1990.

The agricultural chemical composition of the invention can be obtained by compounding the chitosan hydrolyzate having antimicrobial activity and acetic acid in a specified proportion. When the inventive composition containing these ingredients in an adequate proportion is applied to plants, an unexpectedly high synergistic antimicrobial action is exhibited against a large variety of harmful organisms against plants. Accordingly, the present invention can provide an agricultural chemical composition for protecting plants from harmful organisms having a broad antimicrobial spectrum and capable of exhibiting the desired effect even in a very low concentration free from the troubles of chemical injuries to plants. As to the plant-protecting effect against harmful organisms, the optional formulation of the brown juice in the composition consisting of the chitosan hydrolyzate and acetic acid has an advantage of further decreasing the chemical injuries to plants with a consequent possibility of increasing the concentrations of the essential ingredients in the inventive composition so that the plant-protecting effect can be further enhanced. The amount of the brown juice admixed with the composition is not particularly limitative but it is usually in the range from 2% to 20%.

The inventive plant-protecting composition can be used in the form of liquid formulation, dust formulation, granule and the like with adequate admixture of a suitable carrier and other additives. The recipe for use, working concentration and the like of the inventive plant-protecting composition are subject to variation depending on the kind of the phytopathogen and other factors. When the composition is in a liquid form, it is usual that the composition is prepared in such a concentration that the concentration of acetic acid therein is in the range from about 0.002% to about 0.2% by weight in the working solution which is sprayed over the plants to be protected at a suitable interval of, for example, 5 days to 20 days although the exact interval should be selected with reference to the effects obtained by the previous runs of spraying.

Being free from the problem of toxicity against the human body, the plant-protecting composition of the invention can be applied to the fields not only in the seedling and vegetative periods but also at the time of harvesting. This is a very advantageous feature of the inventive composition when it is used in combination with other agricultural chemicals which must be used by strictly following the safety standard for use. For example, it would be a possible recipe to properly use different agricultural chemicals in such a manner that the plant-protecting composition of the invention is used near and in the harvesting time as preceded by the use of another agricultural chemical having higher activity but having toxicity against the human body in the vegetative period so as to decrease the overall amount of use of such a toxic agricultural chemical or to free the harvest from a residual amount of such a toxic agricultural chemical.

In the following, the present invention is described in more detail by way of laboratory-test examples and field-test examples, which, however, never limit the scope of the invention in any way.

Laboratory-test

EXAMPLE 1

(1) Preparation of a chitosan hydrolyzate

A chitosan solution was prepared by dissolving 2 parts by weight of chitosan in 98 parts by weight of an aqueous solution of acetic acid in a concentration of 3% (w/v) and the solution was heated under pressurization at 121° C. for 60 minutes to effect hydrolysis of the chitosan followed by the adjustment of pH of the solution to 5.0 with addition of sodium hydroxide to obtain a hydrolysis product, which is referred to as the chitosan hydrolyzate A hereinbelow.

(2) Preparation of a culture medium containing a chitosan hydrolyzate and acetic acid A PS medium prepared by dispersing and dissolving 200 g of mushed potato and 20 g of sucrose in 1000 ml of distilled water and having a pH of 5.0 was admixed with the chitosan hydrolyzate A prepared above and synthetic acetic acid in such varied proportions that the total amount of the hydrolyzate and acetic acid was always 0.01% by weight, the amount of the chitosan hydrolyzate being calculated relative to the concentration of the chitosan as the starting material, to prepare 6 culture media shown in Table 1 below each having a pH adjusted to 5.0. Each of the culture media was taken in a test tube in a 10 ml portion and subjected to be autoclaved at 121° C. for 15 minutes.

(3) Test of antimicrobial activity

Each of the culture media in a test tube prepared above was inoculated with 0.05 ml of a culture of *Erwinia carotovora* subsp. carotovora IFO 3380 known as a microorganism to cause bacterial soft rot of vegetables, which was obtained by shaking a PS medium inoculated therewith at 30° C. for 24 hours, and shake culture was performed at 30° C. for 156 hours. After the end of this culturing time, the cultures were subjected to the measurement of the optical density (OD) at a wavelength of 660 nm to give a measure for the relative amount of proliferation of the microorganism. The results are shown in Table 1 below.

As is clear from the table, a strong synergistic antimicrobial action was exhibited when the weight proportion of the chitosan hydrolyzate A and acetic acid was in the range from 1:0.25 to 1:4.

TABLE 1

| Chitosan hydrolyzate (A) (%)(w/v) | 0 | 0.002 | 0.004 | 0.006 | 0.008 | 0.01 |
|---|---|---|---|---|---|---|
| Acetic acid (%)(w/v) | 0.01 | 0.008 | 0.006 | 0.004 | 0.002 | 0 |
| Growth of microorganism tested | 0.11 | 0.05 | 0.00 | 0.04 | 0.09 | 0.16 |

TABLE 1-continued (OD at 660 nm)

Laboratory-test

EXAMPLE 2

(1) Preparation of a chitosan hydrolyzate

A solution of chitosan was prepared by adding and dissolving 2 parts by weight of chitosan in 98 parts by weight of a 0.2N hydrochloric acid and the solution was heated at 100° C. for 120 minutes to effect hydrolysis of the chitosan followed by the adjustment of the pH of the solution to 5.0 by the addition of sodium hydroxide to give a hydrolysis product, which is referred to as the chitosan hydrolyzate B hereinbelow.

(2) Preparation of a culture medium containing a chitosan hydrolyzate and vinegar A PSA culture medium prepared by dispersing or dissolving 200 g of mushed potato, 20 g of sucrose and 20 g of agar in 1000 ml of distilled water and having a pH of 5.0 was admixed with the chitosan hydrolyzate B prepared above and a fermented vinegar containing 10% by weight of acetic acid in such varied proportions that the total amount of the chitosan hydrolyzate B and acetic acid was always 0.05%, the amount of the chitosan hydrolyzate B being calculated relative to the concentration of the chitosan as the starting material, to prepare 5 culture media shown in Table 2 below each having a pH adjusted to 5.0. Each of the thus prepared culture media was taken in a test tube in a 10 ml portion and autoclaved at 121° C. for 15 minutes to give a slant culture medium.

(3) Test of antimicrobial activity

Each of the culture media in a test tube prepared above was inoculated with mycelia of *Pythium aphanidermatum* IFO 7030 known to cause spring deadspot and Pythium blight of turfgrass after culturina in a PSA medium at 25° C. for 5 days and culturing thereof was performed at 25° C. for 10 days. After the end of this culturine, time, the cultures were visually examined to find the relative amounts of proliferation of the microorganism. The results are shown in Table 2.

As is clear from the table, a strong synergistic antimicrobial action against the microorganism was exhibited when the mixing ratio of the chitosan hydrolyzate B and acetic acid in the fermented vineger was in the range from 1:0.43 to 1:2.3 by weight.

TABLE 2

| Chitosan hydrolyzate (B) (%)(w/v) | 0 | 0.015 | 0.025 | 0.035 | 0.05 |
|---|---|---|---|---|---|
| Acetic acid (%) (w/v) | 0.05 | 0.035 | 0.025 | 0.015 | 0 |
| Growth of microorganism tested | ++ | + | − | ++ | +++ |

+++: strong growth; ++: medium growth; +: weak growth; −: growth inhibited

Laboratory-test

EXAMPLE 3

(1) Preparation of a chitosan hydrolyzate

A solution of chitosan was prepared by adding and dissolving 2 parts by weight of chitosan in 98 parts by weight of a 0.2N hydrochloric acid and the solution was heated at 100° C. for 120 minutes to effect hydrolysis of the chitosan followed by the adjustment of the pH to 5.0 with addition of sodium hydroxide to give a hydrolysis product, which is referred to as the chitosan hydrolyzate B hereinbelow.

(2) Preparation of a culture medium containing a chitosan

A PSA culture medium having a pH of 5.0 (see Laboratory-test Example 2) was admixed with the chitosan hydrolyzate B and acetic acid in such varied proportions that the total amount of the chitosan hydrolyzate and acetic acid was always 0.05% by weight, the amount of the chitosan hydrolyzate being calculated relative to the concentration of the chitosan as the starting material, to give 5 culture media as shown in Table 3 below each having a pH of 5.0. Each of the culture media was taken in a test tube in a 10 ml portion and autoclaved at 121° C. for 15 minutes to give a slant culture medium.

(3) Test of antimicrobial activity

The slant culture media a prepared above were each inoculated with roycelia of *Rhizoctonia solani* IFO 30464, known to cause spring deadspot, Rhizoctonia large patch and Rhizoctonia brown patch of turfgrass, after culturing in a PSA medium at 25° C. for 5 days and culturing was performed at 25° C. for 10 days. After the end of this culturing time, the cultures were visually examined to find the relative amounts of proliferation of the microorganism. The results are shown in Table 3.

As is clear from the table, a strong synergistic antimicrobial action against the microorganism was exhibited when the mixing ratio of the chitosan hydrolyzate B and the acetic acid in the fermented vinegar was in the range from 1:0.43 to 1:2.3 by weight.

TABLE 3

| Chitosan hydrolyzate (B) (%)(w/v) | 0 | 0.015 | 0.025 | 0.035 | 0.05 |
|---|---|---|---|---|---|
| Acetic acid (%) (w/v) | 0.05 | 0.035 | 0.025 | 0.015 | 0 |
| Growth of microorganism tested | ++ | + | − | + | ++ |

++: medium growth; +: weak growth; −: growth inhibited

Laboratory-test

EXAMPLE 4

(1) Preparation of a chitosan hydrolyzate

A hydrolysis product of chitosan, referred to as the chitosan hydrolyzate B hereinbelow, was prepared in the same manner as in Laboratory-test Example 2.

(2) Preparation of a culture medium containing a chitosan hydrolyzate and vinegar A PSA culture medium having a pH of 5.0 (see Laboratory-test Example 2 ) was admixed with the chitosan hydrolyzate B and vinegar in such varied proportions that the total amount of the chitosan hydrolyzate B and acetic acid in the vinegar was always 0.1% by weight, the amount of the chitosan hydrolyzate being calculated relative to the concentration of the chitosan as the starting material, to give 6 culture media each having a pH of 5.0. The culture media were each taken in a test tube in a 10 ml portion and autoclaved at 121° C. for 15 minutes to give a slant culture medium.

(3) Test of antimicrobial activity

The above prepared slant culture media were each inoculated with mycelia of *Helminthosporium sacchari* IFO 9283, known to cause Helminthosporium leaf blight of turfgrass, after culturing in a PSA medium at 25° C. for 5 days and culturing was performed at 25° C. for 10 days. After the end of this culturing time, the cultures were visually examined to find the relative amounts of growth of the microorganism. The results are shown in Table 4 below.

As is clear from the table, a strong synergistic antimicrobial action against the microorganism was exhibited when the mixing ratio of the chitosan hydrolyzate and acetic acid in the vinegar was in the range from 1:0.25 to 1:4 by weight.

TABLE 4

| Chitosan hydrolyzate (B) (%)(w/v) | 0 | 0.02 | 0.04 | 0.06 | 0.08 | 0.1 |
|---|---|---|---|---|---|---|
| Acetic acid (%) (w/v) | 0.1 | 0.08 | 0.06 | 0.04 | 0.02 | 0 |
| Growth of microorganism tested | +++ | ++ | − | ++ | ++ | +++ |

+++: strong growth; ++: medium growth; +: weak growth; −: growth inhibited

Laboratory-test

EXAMPLE 5

(1) Preparation of a chitosan hydrolyzate

A solution of chitosan was prepared by dissolving 5.0 g of chitosan in 100 ml of an aqueous solution of lactic acid in a 2% (w/v) concentration. The solution was admixed with 0.2 g of an enzyme preparation Macerozyme 2S and gently agitated for 6 hours at 45° C. to effect enzymatic decomposition of the chitosan. After the end of this reaction time, the vessel containing the reaction mixture was kept for 5 minutes in boiling water to inactivate the enzyme followed by the adjustment of the pH to 5.0 with addition of sodium hydroxide to give a hydrolysis product of chitosan, which is referred to as the chitosan hydrolyzate C hereinbelow.

(2) Preparation of an acetic acid-containing solution

One liter of a fermented vinegar containing 10% by weight of acetic acid was admixed with 30 g of eggshell powder, 14.0 g of sodium hydrogencarbonate and 6.67 g of sodium hydroxide to be partially neutralized. The thus prepared solution contained 5% by weight of acetic acid.

(3) Preparation of a culture medium containing a chitosan hydrolyzate and acetic acid A PS culture medium having a pH of 5.0 (see Laboratory-test Example 1) was admixed with the chitosan hydrolyzate C prepared in (1) above and the acetic acid-containing solution prepared in (2) above in such varied proportions that the total amount of the chitosan hydrolyzate C and acetic acid in the acetic acid-containing solution was always 0.05% by weight, the amount of the chitosan hydrolyzate being calculated relative to the concentration of the chitosan as the starting material, to give 5 culture media shown in Table 5 below each having a pH of 5.0. The thus prepared culture media were each taken in a test tube in a 10 ml portion and autoclaved at 121° C. for 15 minutes.

(4) Test of antimicrobial activity

The above prepared culture media were each inoculated with 0.05 ml of a liquid culture of Pseudomonas glumae ARB 6021007, known to cause bacterial grain rot of rice, after shake culturing in a PS medium at 30° C. for 24 hours and shake culturing was performed at 30° C. for 48 hours. After this culturing time, the cultures were subjected to the measurement of the optical density at a wavelength of 660 nm to make a relative comparison of the growth amounts of the microorganism. The results are shown in Table 5 below.

As is clear from the table, a strong synergistic antimicrobial action against the microorganism was exhibited when the mixing ratio of the chitosan hydrolyzate C and acetic acid in the acetic acid-containing solution was in the range from 1:0.43 to 1:2.3 by weight.

TABLE 5

| Chitosan hydrolyzate (C) (%)(w/v) | 0 | 0.015 | 0.025 | 0.035 | 0.05 |
|---|---|---|---|---|---|
| Acetic acid (%)(w/v) | 0.05 | 0.035 | 0.025 | 0.015 | 0 |
| Growth of microorganism tested (OD at 660 nm) | 0.54 | 0.03 | 0.00 | 0.00 | 0.27 |

Laboratory-test

EXAMPLE 6

(1) Preparation of a chitosan hydrolyzate

A solution of chitosan was prepared by dissolving 5.0 g of chitosan in 100 ml of a commercial product of vinegar containing 4.2% (w/v) of acetic acid. The solution was admixed with 0.1 g of an enzyme preparation Sumyzyme AP2 and gently agitated for 6 hours at 50° C. to effect enzymatic decomposition of the chitosan. After the end of this reaction time, the vessel containing the reaction mixture was kept for 5 minutes in boiling water to inactivate the enzyme followed by the adjustment of the pH to 5.0 to prepare a hydrolysis product of chitosan, which is referred to as the chitosan hydrolyzate D hereinbelow.

(2) Preparation of an acetic acid-containing solution

An acetic acid-containing solution, of which the concentration of acetic acid was 5% by weight, was prepared in the same manner as described in (2) of Laboratory-test Example 5.

(3) Preparation of a culture medium containing a chitosan hydrolyzate and acetic acid A PSA culture medium having a pH of 5.0 (see Laboratory-test Example 2) was admixed with the chitosan hydrolyzate D prepared in (1) above and the acetic acid-containing solution prepared in (2) above in such varied proportions that the total amount of the chitosan hydrolyzate D and the acetic acid in the acetic acid-containing solution was always 0.1% by weight, the amount of the chitosan hydrolyzate being calculated relative to the concentration of the chitosan as the starting material to give 6 culture media as shown in Table 6 below each having a pH of 5.0. The thus prepared culture media were each taken in a test tube in a 10 ml portion and autoclaved at 121° C. for 15 minutes to give a slant culture medium.

(4) Test of antimicrobial activity

The slant culture media prepared above were each inoculated with mycelia of Cladosporium carpophilum IFO 9645, known to cause scab of fruit trees, after culturing in a PSA medium at 25° C. for 5 days and culturing was performed at 25° C. for 10 days. After the end of this culturing time, the cultures were visually examined to find the relative amounts of growth of the microorganism. The results are shown in Table 6 below.

As is clear from the table, a strong synergistic antimicrobial action was exhibited when the mixing ratio of the chitosan hydrolyzate D and acetic acid in the acetic acid-containing solution was in the range from 1:0.25 to 1:4 by weight.

TABLE 6

| Chitosan hydrolyzate (D) (%)(w/v) | 0 | 0.02 | 0.04 | 0.06 | 0.08 | 0.1 |
|---|---|---|---|---|---|---|
| Acetic acid (%)(w/v) | 0.1 | 0.08 | 0.06 | 0.04 | 0.02 | 0 |
| Growth of micro- | ++ | − | ++ | ++ | ++ | +++ |

TABLE 6-continued organism tested

+++: strong growth; ++: medium growth; +: weak growth; —: growth inhibited

Laboratory-test

EXAMPLE 7

(1) Preparation of a chitosan hydrolyzate

A hydrolysis product of chitosan, referred to as the chitosan hydrolyzate C hereinbelow, was prepared in the same manner as in (1) of Laboratory-test Example 5 described above.

(2) Preparation of an acetic acid-containing solution

An acetic acid-containing solution, of which the concentration of acetic acid was 5% by weight, was prepared in the same manner as in (2) of Laboratory-test Example 5 described above.

(3) Preparation of a brown juice

Fresh alfalfa as reamed was squeezed in a squeezer to obtain green juice. Steam at a temperature of 130° C. was blown into this green juice to coagulate the proteinaceous material therein followed by centrifugal separation of the coagulum to obtain a brown juice.

(4) Preparation of a plant-protecting composition containing a chitosan hydrolyzate, acetic acid and brown juice A plant-protecting composition, referred to as the composition A hereinbelow, was prepared by mixing 2 parts by weight of the chitosan hydrolyzate C prepared in (1) above, 3 parts by weight of the acetic acid-containing solution prepared in (2) above and 0.5 part by weight of pure water.

Another plant-protecting composition, referred to as the composition B hereinbelow, was prepared in the same formulation as above excepting replacement of pure water with the same amount of the brown juice prepared in (3) above.

(5) Preparation of culture media containing the plant-protecting composition

A PSA culture medium was admixed with the above prepared composition A or B in varied amounts followed by the adjustment of the pH to 5.0. The thus prepared culture media were taken in test tubes each in a 10 ml portion and autoclaved at 121° C. for 15 minutes to give slant culture media.

(6) Test of antimicrobial activity

The slant culture media prepared above were each inoculated with a microorganism, which was either a phytopathogenic fungus after culturing in a PSA medium at 25° C. for 5 days or a phytopathogenic bacterium after culturing in a PSA medium at 30° C. for 24 hours, and culturing was performed for 10 days at 25° C. for the phytopathogenic fungi or at 30° C. for the phytopathogenic bacteria. After the end of this culturing time, the cultures were visually examined for the growth condition of the microorganism to determine the minimal inhibitory concentration (MIC) of the plant-protecting composition in % by weight.

The species of the microorganisms tested and the principal plant diseases caused thereby are as shown below.

Phytopathogenic fungi

*Botryotinia fuckeliana* IFO 5365: gray mold of vegetables, fruits and flowers

*Botrytis cinerea* IFO 31831: gray mold of vegetables, fruits and flowers

*Cladosporium carpophilum* IFO 9645: scab of peaches, plums, apricots, Japanese apricots and cherrys

*Fulvia fulva* IFO 8419: blue mold of tomato

*Fusarium oxysporum* IFO 7152: yellows of Japanese radish and cabbage; stem rot of cucumber and melon; Fusarium wilt of tomato

*Fusarium roseum* f. sp. cerealis IFO 9978: scab of barleys and wheats; spring deadspot of turfgrass; damping-off of rice

*Pythium aphanidermatum* IFO 7030: Pythium fruit rot of tomato, cucumber and pumpkin; spring deadspot of turfgrass; Pythium blight of turfgrass

*Rhizoctonia solani* IFO 30464: damping-off of cucumber, egg plant, cabbage, Chinese cabbage and Welsh onion; root rot of carrot and yam; Rhizoctonia brown patch of turfgrass; Rhizoctonia large patch of turfgrass; spring deadspot of turfgrass

*Gibberella fujikuroi* IFO 30336: "Bakanae" disease of rice; scab of Indian corn

*Sclerotinia sclerotiorum* IFO 4876: sclerotial rot of cucumber, tomato, egg plant, green pepper, lettuce and strawberry

*Valsa ceratosperma* IFO 30252: canker of apple; dieback of rose

*Helminthosporium sacchari* IFO 9283: Helminthosporium leaf blight of turfgrass; Eye spot of sugar cane Phytopathogenic bacteria

*Agrobacteriura rhizogenes* A4: Hairy root of apple

*Corynebacterium michiganense* IFO 12471: bacterial canker of tomato

*Erwinia carotovora* subsp. carotovora IFO 3380: bacterial soft rot of vegetables

*Pseudomonas syringae* pv. lachrymans NIAES 1318: bacterial blight of cucumber

*Xanthomonas campestris* pv. oryzae NIAES 1226: bacterial leaf blight of rice

*Pseudomonas glumae* ARB 60201007: bacterial grain rot of rice

The results are shown in Table 7 below. As is clear from this table, the plant-protecting compositions A and B of the present invention each had a very broad antimicrobial spectrum and exhibited very strong antimicrobial action against all of the phytopathogenic fungi and bacteria used for the tests. This fact suggests applicability of the present invention not only to plant diseases but also to other diseases in a very wide range.

Although the results in Table 7 indicate that admixture of the brown juice had absolutely no influences on the antimicrobial action of the plant-protecting compositions, a remarkable beneficial effect can be obtained thereby when the plant-protecting composition of the invention is used in field tests using living plant bodies in which the damages due to chemicals can be greatly reduced.

TABLE 7

| Phytopathogenic microorganism | MIC (%) Plant-protecting composition (A) | Plant-protecting composition (B) |
| --- | --- | --- |
| *Botryotinia fuckeliana* IFO 5365 | 3.2 | 3.2 |
| *Botrytis cinerea* IFO 31831 | 3.2 | 3.2 |
| *Cladosporium carpophilum* IFO 9645 | 3.2 | 3.2 |
| *Fulvia fulva* IFO 8419 | 0.4 | 0.4 |
| *Fusarium oxysporum* IFO 7152 | 3.2 | 3.2 |
| *Fusarium roseum* f. sp. *cerealis* IFU-9978 | 1.6 | 1.6 |
| *Pythium aphanidermatum* IFO 7030 | 1.6 | 1.6 |

TABLE 7-continued

| Phytopathogenic microorganism | MIC (%) Plant-protecting composition (A) | Plant-protecting composition (B) |
|---|---|---|
| *Rhizoctonia solani* IFO 30464 | 1.6 | 1.6 |
| *Sclerotinia sclerotiorum* IFO 4876 | 1.6 | 1.6 |
| *Valsa ceratosperma* IFO 30252 | 0.8 | 0.8 |
| *Gibberella fujikuroi* IFO 30336 | 0.1 | 0.1 |
| *Helminthosporium sacchari* IFO 9283 | 3.2 | 3.2 |
| *Agrobacterium rhizogenes* A4 | 0.2 | 0.2 |
| *Corynebacterium michiganense* IFO 12471 | 0.2 | 0.2 |
| *Erwinia carotovora* subsp. *carotovora* IFO 3380 | 0.1 | 0.1 |
| *Pseudomonas syringae* pv. *lachrymans* NIAES 1318 | 0.1 | 0.1 |
| *Xanthomonas campestris* pv. *oryzae* NIAES 1226 | 0.8 | 0.8 |
| *Pseudomonas glumae* ARB 60201007 | 1.6 | 1.6 |

Field-test

EXAMPLE 1

(1) Preparation of a chitosan hydrolyzate

A hydrolysis product of chitosan, referred to as the chitosan hydrolyzate B hereinbelow, was prepared in the same manner as in (1) of Laboratory-test Example 2 described above.

(2) Preparation of an acetic acid-containing solution

An acetic acid-containing solution was prepared in the same manner as in (2) of Laboratory-test Example 5 described above.

(3) Preparation of a brown juice

A brown juice was prepared in the same manner as in (3) of Laboratory-test Example 7.

(4) Preparation of a plant-protecting composition of the present invention

A plant-protecting composition of the present invention, referred to as the composition C hereinbelow, was prepared by mixing 4 parts by weight of the chitosan hydrolyzate B prepared in (1) above, 0.5 part by weight of a fermented vinegar containing 10% by weight of acetic acid and 1 part by weight of pure water.

Another plant-protecting composition of the invention, referred to as the composition D hereinbelow, was prepared by mixing 4 parts by weight of the chitosan hydrolyzate B prepared in (1) above, 1 part by weight of the acetic acid-containing solution prepared in (2) above and 0.5 part by weight of pure water.

A further plant-protecting composition, referred to as the composition E hereinbelow, was prepared by mixing 4 parts by weight of the chitosan hydrolyzate B prepared in (1) above, 1 part by weight of the acetic acid-containing solution prepared in (2) above and 0.5 part by weight of the brown juice prepared in (3) above.

(5) Tests for plant-disease control and chemical injuries i) Plant disease tested: bacterial soft rot of Chinese cabbage ii) Strain of the vegetable: "akogare:

iii) Type of growing: outdoor growing; seeding Aug. 3, 1989; permanent setting of seedlings Aug. 17, 1989 iv) Testing zone: 20 plants/zone v) Application of plant-protecting compositions: working solutions were prepared by diluting the compositions C, D and E prepared in (4) above each by 5 times, 50 times, 150 times and 400 times and applicated 3 times on Sep. 11, 18 and 25, 1989 in a volume of 400 l per 10 ares by using a shoulder-carried full-automatic spraying machine vi) Inspection: once on Oct. 2, 1989 vii) Results

As is shown in Table 8, appearance of the bacterial soft rot of Chinese cabbage could be prevented by the application of the 15 to 400 times-diluted working solutions of the inventive plant-protecting compositions C, D and E. The effect was more remarkable when the concentration of the working solution was higher though with an increase in the chemical injury. The chemical damage was less significant by using the composition D prepared by mixing the chitosan hydrolyzate and the acetic acid-containing solution as compared with the composition C prepared with pure acetic acid. Alleviation of the chemical injury was prominent by using the composition E prepared with the brown juice in place of pure water. Absence of the chemical injury even in the zone under application of the 15 times-diluted solution, where the preventive value was high, supports the high practical value of the composition E in the prevention of bacterial soft rot of vegetables.

TABLE 8

| | Dilution, times | Number inspected | Proportion of diseased plant (%) | Disease severity | Preventive value | Chemical injuries |
|---|---|---|---|---|---|---|
| Control | — | 60 | 78.3 | 51.1 | | |
| Plant-protecting composition (C) | 15 | 60 | * | * | * | + |
| | 50 | 60 | 34.5 | 23.4 | 54.3 | + |
| | 150 | 60 | 46.4 | 30.6 | 40.2 | ± |
| | 400 | 60 | 59.8 | 44.4 | 13.2 | — |
| Plant-protecting composition (D) | 15 | 60 | 30.2 | 15.6 | 69.5 | ± |
| | 50 | 60 | 35.4 | 23.7 | 53.6 | ± |
| | 150 | 60 | 43.6 | 30.9 | 39.6 | — |
| | 400 | 60 | 57.2 | 43.5 | 14.8 | — |
| Plant-protecting composition (E) | 15 | 60 | 31.2 | 16.5 | 67.8 | ± |
| | 50 | 60 | 36.5 | 24.1 | 52.9 | — |
| | 150 | 60 | 42.1 | 29.0 | 43.3 | — |

TABLE 8-continued

| Dilution, times | Number inspected | Proportion of diseased plant (%) | Disease severity | Preventive value | Chemical injuries |
|---|---|---|---|---|---|
| 400 | 60 | 58.9 | 44.5 | 12.9 | — |

Chemical injuries:
—; no chemical injuries found
±; chemical injuries found but no problem in practical application
+; practical detrimental chemical injuries found
*Inspection of the disease severity and other items could not be undertaken in the zone where the 15-times diluted solution of the plant-protecting composition C due to heavy wilt.
%, proportion of diseased plant = (number of diseased plants)/(number of inspected plants) × 100
disease severity = Σ (number of diseased plants in each degree × factor)/(number of inspected plants) × 100 factors
0: no diseased
1: diseased limited to a part of outer leaves
2: diseased found in outer leaves and a part of head leaves
3: diseased found in most of head leaves, or withering
preventive value = (disease severity in control zone - disease severity in test zone)/(disease severity in control zone) × 100

Field-test

EXAMPLE 2

(1) Preparation of a chitosan hydrolyzate

A hydrolysis product of chitosan, referred to as the chitosan hydrolyzate A hereinbelow, was prepared in the same manner as in (1) of Laboratory-test Example 1.

(2) Preparation of an acerbic acid-containing solution

An acetic acid-containing solution was predated in the same manner as in (2) of Laboratory-test Example 5.

(3) Preparation of a brown juice

A brown juice was prepared in the same manner as in (3) of Laboratory-test Example 7.

(4) Preparation of plant-protecting compositions

A plant-protecting composition, referred to as the composition F hereinbelow, was prepared by mixing 4 parts by weight of the chitosan hydrolyzate A prepared in (1) above, 0.5 part by weight of a fermented vinegar containing 10% by weight of acetic acid and 1 part by weight of pure water.

Another plant-protecting composition, referred to as the composition G hereinbelow, was prepared by mixing 4 parts by weight of the chitosan hydrolyzate A prepared in (1) above, 1 part by weight of the acetic acid-containing solution prepared in (2) above and 0.5 part by weight of pure water.

A further plant-protecting composition, referred to as the composition H hereinbelow, was prepared by mixing 4 parts by weight of the chitosan hydrolyzate A prepared in (1) above, 1 part by weight of the acetic acid-containing solution prepared in (2) above and 0.5 part by weight of the brown juice prepared in (3) above.

(5) Tests for plant-disease control and chemical injuries
 i) Plant disease tested: spring deadspot of turfgrass
 ii) Strain of turfgrass: "manillagras"
 iii) Testing zone: 20 m² within the area of frequent occurrence of the disease last year
 iv) Application of the plant-protecting compositions: working solutions were prepared by diluting the compositions F, G and H prepared in (4) above each by 5 times, 15 times, 50 times and 150 times and applicated 10 times in every 2 weeks during the period beginning with Nov. 2, 1989 and ending with Mar. 13, 1990 in a volume of 1 liter per m² area by using a power spray machine.
 v) Inspection: twice on Mar. 28 and Apr. 19, 1990
 vi) Results As is shown in Table 9, appearance of the spring dead-spot in turfgrass could be suppressed by using the inventive plant-protecting compositions F, G and H when the working solutions were prepared by 5 times to 50 times dilution. Although chlorosis of some leaves was found in the zones where the concentration of the applicated solution was high like in Field-test Example 1, the morbidness was less significant in the zone where the composition G prepared by mixing the chitosan hydrolyzate and the acetic acid-containing solution than the composition F. Chemical injury was not found, however, even in the zone where a high preventive value could be obtained by using a 5 times-diluted solution of the composition H prepared by the addition of the brown juice in place of pure water. This result supports the conclusion that the composition H has a high practical value as an agent for the control of spring deadsport of turfgrass.

TABLE 9

| | | March 28, 1990 | | April 19, 1990 | | |
|---|---|---|---|---|---|---|
| | Dilution, times | % of diseased area | Preventive value | % of diseased area | Preventive value | Chemical injuries |
| Control | — | 2.81 | — | 18.3 | — | — |
| Plant-protecting composition (I) | 5 | 0.90 | 67.9 | 6.94 | 62.1 | ± |
| | 15 | 1.17 | 58.2 | 8.11 | 55.7 | — |
| | 50 | 1.60 | 42.9 | 11.2 | 38.8 | — |
| | 150 | 1.91 | 32.1 | 12.8 | 29.8 | — |
| Plant-protecting composition (G) | 5 | 1.01 | 63.9 | 7.58 | 58.6 | ± |
| | 15 | 1.30 | 53.6 | 9.48 | 48.2 | — |
| | 50 | 1.32 | 43.2 | 11.1 | 39 6 | — |
| | 150 | 1.81 | 35.7 | 12.0 | 34:2 | — |
| Plant-protecting composition (H) | 5 | 1.00 | 64.3 | 6.81 | 62.8 | — |
| | 15 | 1.33 | 52.6 | 8.31 | 54.6 | — |
| | 50 | 1.71 | 39.3 | 10.2 | 44.3 | — |

TABLE 9-continued

| Dilution, times | March 28, 1990 | | April 19, 1990 | | Chemical injuries |
|---|---|---|---|---|---|
| | % of diseased area | Preventive value | % of diseased area | Preventive value | |
| 150 | 1.90 | 32.4 | 12.6 | 31.3 | — |

Chemical injuries:
—; no chemical injuries found
±; chemical injuries found but no problem in practical application
%, diseased area = (patched area in testing zone)/(testing zone) × 100
preventive value = (diseased area in control zone - diseased area in test zone)/(diseased area in control zone) × 100

Field-test

EXAMPLE 3

(1) Preparation of a chitosan hydrolyzate

A hydrolysis product of chitosan, referred to as the chitosan hydrolyzate A hereinbelow, was prepared in the same manner as in (1) of Laboratory-test Example 1.

(2) Preparation of an acetic acid-containing solution

An acetic acid-containing solution was prepared in the same manner as in (2) of Laboratory-test Example 5.

(3) Preparation of a brown juice

A brown juice was prepared in the same manner as in (3) of Laboratory-test Example 7.

(4) Preparation of plant-protecting compositions

Plant-protecting compositions F, G and H were prepared each with the same formulation as in (4) of Field-test Example 2 described above.

(5) Tests for plant disease prevention and chemical damages i) Plant disease tested: Rhizoctonia large patch of turfgrass
ii) Strain of turfgrass: "manillagrass"
iii) Testing zone: 150 m²
iv) Application of the plant-protecting compositions: working solutions were prepared by diluting the compositions F, G and H prepared in (4) above each by 5 times, 15 times, 50 times and 150 times and applicated 6 times in every 2 weeks during the period beginning with Jan. 18 and ending with Mar. 30, 1990 in a volume of 1 liter per m² area by using a power spraying machine.
v) Inspection: twice on Apr. 5 and Apr. 26, 1990
vi) Results As is shown in Table 10, appearance of Rhizoctonia large patch in turfgrass could be controlled by using the solutions prepared by the 5 times to 150 times dilution of the inventive compositions F, G and H. Practically permissible chlorosis was found in several leaves in the zones where a high concentration solution was applicated. The morbidness of chlorosis was less significant with the solutions prepared from the composition G prepared by mixing the chitosan hydrolyzate and the acetic acid-containing solution than the composition F and no chemical injury was found with the composition H prepared by using the brown juice in place of pure water. This result supports the practical usefulness of the composition H to give a high preventive value without chemical injuries as a preventing agent against Rhizoctonia large patch of turfgrass.

TABLE 10

| | Dilution, times | April 5, 1990 | | April 26, 1990 | | Chemical injuries |
|---|---|---|---|---|---|---|
| | | % of diseased area | Preventive value | % of diseased area | Preventive value | |
| Control | — | 3.24 | — | 18.3 | — | — |
| Plant-protecting composition (F) | 5 | 1.19 | 63.2 | 10.5 | 64.8 | ± |
| | 15 | 1.42 | 56.3 | 13.5 | 54.6 | — |
| | 50 | 1.82 | 43.7 | 17.8 | 40.3 | — |
| | 150 | 2.32 | 28.4 | 21.0 | 29.6 | — |
| Plant-protecting composition (G) | 5 | 1.24 | 61.8 | 11.3 | 62.1 | ± |
| | 15 | 1.51 | 53.5 | 14.1 | 52.8 | — |
| | 50 | 1.89 | 41.6 | 18.3 | 38.6 | — |
| | 150 | 2.26 | 30.2 | 21.5 | 27.8 | — |
| Plant-protecting composition (H) | 5 | 1.03 | 68.1 | 10.9 | 63.4 | — |
| | 15 | 1.42 | 56.3 | 15.0 | 49.8 | — |
| | 50 | 1.82 | 43.8 | 17.1 | 42.6 | — |
| | 150 | 2.27 | 29.8 | 20.5 | 31.2 | — |

Chemical injuries:
—; no chemical injuries found
±; chemical injuries found but no problem in practical application Field-test

EXAMPLE 4

(1) Preparation of a chitosan hydrolyzate

A hydrolysis product of chitosan, referred to as the chitosan hydrolyzate A hereinbelow, was prepared in the same manner as in (1) of Laboratory-test Example 1.

(2) Preparation of an acetic acid-containing solution

An acetic acid-containing solution was prepared in the same manner as in (2) of Laboratory-test Example 5.

(3) Preparation of a brown juice

A brown juice was prepared in the same manner as in (3) of Laboratory-test Example 7.

(4) Preparation of plant-protecting compositions

Plant-protecting compositions F, G and H were prepared each in the same formulation as in (4) of Field-test Example 2 described above.

A further plant-protecting composition, referred to as the composition I hereinbelow, was prepared by mixing 4 parts by weight of the chitosan hydrolyzate A prepared in (1) above, 0.5 part by weight of a fermented vinegar containing 10% by weight of acetic acid, 0.5 part by weight of pure water and 0.5 part by weight of the brown juice prepared in (3) above.

(5) Tests of plant-disease control and chemical injuries i) Plant disease tested: Helminthosporium leaf blight of turfgrass
ii) Strain of turfgrass: "manillagrass"
iii) Testing zone: 4 m² within the area of frequent occurrence of the disease last year
iv) Application of the plant-protecting composition: working solutions were prepared by diluting the compositions F, G, H and I each by 5 times, 15 times, 50 times and 150 times and applicated 6 times in every 2 weeks during the period beginning with Mar. 24 and ending with Jun. 7, 1989 in a volume of 1 liter per m² area using a watering pot.
v) Inspection: once on Jun. 21, 1989
vi) Results As is shown in Table 11, appearance of Helminthosporium leaf blight in turfgrass could be controlled by using the solutions prepared by the 5 times to 150 times dilution of the inventive plant-protecting compositions F, G, H and I. Chemical injuries of slight chlorosis of leaves were found in the zones where a high concentration solution of the composition F or G was used. No chemical injuries were found in the zones where the applicated solutions were prepared from the compositions H and I with admixture of the brown juice. This result supports the practical usefulness of the compositions H and I as a preventing agent against Helminthosporium leaf blight of turfgrass to give a high preventive value without chemical injuries.

TABLE 11

|  | Dilution, times | % of diseased area | Preventive value | Chemical injuries |
|---|---|---|---|---|
| Control | — | 4.63 | — | — |
| Plant-protecting composition (F) | 5 | 1.53 | 67.0 | ± |
|  | 15 | 2.66 | 42.5 | — |
|  | 50 | 2.79 | 39.7 | — |
|  | 150 | 3.39 | 26.8 | — |
| Plant-protecting composition (G) | 5 | 1.66 | 64.1 | ± |
|  | 15 | 2.10 | 54.6 | — |
|  | 50 | 2.85 | 38.5 | — |
|  | 150 | 3.54 | 23.6 | — |
| Plant-protecting composition (H) | 5 | 1.65 | 64.4 | — |
|  | 15 | 2.46 | 46.8 | — |
|  | 50 | 2.89 | 37.5 | — |
|  | 150 | 3.77 | 18.6 | — |
| Plant-protecting composition (I) | 5 | 1.60 | 65.4 | — |
|  | 15 | 2.45 | 47.1 | — |
|  | 50 | 2.95 | 36.2 | — |
|  | 150 | 3.58 | 22.6 | — |

Chemical injuries:
—; no chemical injuries found
±; chemical injuries found but no problem in practical application Field-test

EXAMPLE 5

(1) Preparation of a chitosan hydrolyzate
A hydrolysis product of chitosan, referred to as the chitosan hydrolyzate A hereinbelow, was prepared in the same manner as in (1) of Laboratory-test Example 1.
(2) Preparation of an acetic acid-containing solution
An acetic acid-containing solution was prepared in the same manner as in (2) of Laboratory-test Example 5.
(3) Preparation of a brown juice
A brown juice was prepared in the same manner as in (3) of Laboratory-test Example 7.
(4) Preparation of plant-protecting compositions
Plant-protecting compositions F, G and H were prepared each in the same formulation as in Field-test Example 2 described above.
(5) Tests of plant-disease control and chemical injuries
i) Plant disease tested: Rhizoctonia brown patch of turfgrass
ii) Strain of turfgrass: "bentgrass"
iii) Testing zone: trinity of 2 m² zones
iv) Application of the plant-protecting composition: working solutions were prepared by diluting the compositions F, G and H prepared in (4) above each by 5 times, 15 times, 50 times and 150 times and applicated 4 times in every 7 days during the period beginning with Jun. 18 and ending with Jul. 9, 1990 in a volume of 1 liter per m² area by using a watering pot.
v) Inspection: twice on Jul. 9 and Jul. 16, 1990
vi) Results As is shown in Table 12, appearance of Rhizoctonia brown patch in turfgrass could be controlled by using the 5 times to 150 times diluted solutions of the compositions F, G and H. Slight chlorosis of leaves of practically permissible degree was found in the zones where a high concentration solution was applicated. Morbidness of chlorosis was less significant in the zones where application was performed of the solutions prepared from the composition G by the admixture of the chitosan hydrolyzate A and the acetic acid-containing solution and not found in the zones where application was performed of the solutions prepared from the composition H in which the brown juice was admixed. This result supports the practical usefulness of the composition H to give a high preventive value without chemical injuries as a preventing agent against Rhizoctonia brown patch of turfgrass.

TABLE 12

|  |  | July 9, 1990 | | July 16, 1990 | | |
|---|---|---|---|---|---|---|
|  | Dilution, times | % of diseased area | Preventive value | % of diseased area | Preventive value | Chemical injuries |
| Control | — | 30.3 | — | 37.6 | — | — |
| Plant-protecting composition (F) | 5 | 3.18 | 89.5 | 4.17 | 88.9 | ± |
|  | 15 | 5.85 | 80.7 | 7.71 | 79.5 | — |
|  | 50 | 7.51 | 75.2 | 10.5 | 72.1 | — |
|  | 150 | 13.4 | 55.8 | 18.3 | 51.3 | — |
| Plant-protecting composition (G) | 5 | 3.45 | 88.6 | 6.17 | 83.6 | ± |
|  | 15 | 4.45 | 85.3 | 7.14 | 81.0 | — |
|  | 50 | 9.24 | 69.5 | 14.9 | 60.3 | — |
|  | 150 | 13.0 | 57.1 | 18.7 | 50.3 | — |
| Plant-protecting composition (H) | 5 | 1.94 | 93.6 | 5.19 | 86.2 | — |
|  | 15 | 3.00 | 90.1 | 7.33 | 80.5 | — |
|  | 50 | 4.79 | 84.2 | 13.1 | 65.2 | — |

TABLE 12-continued

| Dilution, times | July 9, 1990 | | July 16, 1990 | | Chemical injuries |
|---|---|---|---|---|---|
| | % of diseased area | Preventive value | % of diseased area | Preventive value | |
| 150 | 8.97 | 70.4 | 13.4 | 64.4 | — |

Chemical injuries:
—; no chemical injuries found
±; chemical injuries found but no problem in practical application Field-test

EXAMPLE 6

(1) Preparation of a chitosan hydrolyzate

A hydrolysis product of chitosan, referred to as the chitosan hydrolyzate A hereinbelow, was prepared in the same manner as in (1). of Laboratory-test Example 1.

(2) Preparation of an acetic acid-containing solution

An acetic acid-containing solution was prepared in the same manner as in (2) of Laboratory-test Example 5.

(3) Preparation of a brown juice

A brown juice was prepared in the same manner as in (3) of Laboratory-test Example 7.

(4) Preparation of plant-protecting compositions

Plant-protecting compositions F, G and H were prepared each in the same formulation as in Field-test Example 2 described above.

(5) Tests of plant disease control and chemical injuries
 i) Pest tested: larvae of lawn grass cutworm
 ii) Testing zone: mix-sod turf of "manillagrass" and Japanese lawngrass, 16 m² within the area of frequent occurence of the pest injury last year.
 iii) Application of the plant-protecting composition: working solutions were prepared by diluting the compositions F, G and H prepared in (4) above each by 5 times, 15 times, 50 times, 150 times and 400 times and applicated 8 times in every 10 days during the period beginning with Mar. 22 and ending with Jun. 7, 1989 in a volume of 1 liter per m² area by using a shoulder-carried full-automatic spraying machine.
 iv) Inspection: three times on Mar. 20, Jun. 14 and Jun. 21, 1989
 v) Results As is shown in Table 13, development of larvae of lawn grass cutworm could be suppressed by using the solutions prepared by 5 times to 400 times dilution of the compositions F, G and H. Chlorosis of the leaves in a slight and practically permissible degree was found in the zones where a high concentration solution was applicated. Such a chemical injury was not found in the zones where the solution applicated was prepared from the composition H by the admixture of the brown juice. The results also support the effectiveness of the compositions F, G and H for the extermination of the larvae of lawn grass cutworm. Further, a decrease was noted in the testing zones in the number of larvae of pale brownish chafer indicating broader applicability of the inventive composition also to the extermination of this pest.

TABLE 13

| | Dilution, times | March 20, 1989 Average number of live larvae | June 14, 1989 | | June 21, 1989 | | Chemical injuries |
|---|---|---|---|---|---|---|---|
| | | | Average number of live larvae | Density index after correction | Average number of live larvae | Density index after correction | |
| Control | — | 8.00 | 204.7 | | 135.9 | | |
| Plant-protecting composition (F) | 5 | 8.80 | 55.3 | 24.6 | 38.1 | 25.5 | ± |
| | 15 | | 67.6 | 30.0 | 42.9 | 28.7 | — |
| | 50 | | 86.1 | 38.2 | 59.3 | 39.7 | — |
| | 150 | | 102.6 | 45.6 | 67.5 | 45.2 | — |
| | 400 | | 126.8 | 56.3 | 95.3 | 63.8 | — |
| Plant-protecting composition (G) | 5 | 7.86 | 53.8 | 26.8 | 40.1 | 30.0 | ± |
| | 15 | | 70.2 | 34.9 | 43.6 | 32.7 | — |
| | 50 | | 82.9 | 41.2 | 61.7 | 46.2 | — |
| | 150 | | 100.3 | 49.9 | 64.8 | 48.5 | — |
| | 400 | | 138.6 | 68.9 | 93.8 | 70.3 | — |
| Plant-protecting composition (H) | 5 | 9.12 | 60.8 | 26.1 | 36.2 | 23.4 | ± |
| | 15 | | 64.5 | 27.6 | 41.8 | 27.0 | — |
| | 50 | | 89.3 | 38.3 | 63.6 | 41.1 | — |
| | 150 | | 98.6 | 42.3 | 70.2 | 45.3 | — |
| | 400 | | 137.8 | 59.1 | 98.6 | 63.6 | — |

Chemical injuries:
—; no chemical injuries found
±; chemical injuries found but no problem in practical application
Density index after correction = [(average number of live larvae after applicating of solution in treated zone) × (average number of live larvae before applicating of solution in control zone)]/[(average number of live larvae before applicating of solution in treated zone) × (average number of live larvae after applicating of solution in control zone)] × 100

Field-test

EXAMPLE 7

(1) Preparation of a chitosan hydrolyzate

A hydrolysis product of chitosan, referred to as the chitosan hydrolyzate D hereinbelow, was prepared in the same manner as in (1) of Laboratory-test Example 6.

(2) Preparation of an acetic acid-containing solution

An acetic acid-containing solution was prepared in the same manner as in (2) of Laboratory-test Example 5.

(3) Preparation of a brown juice

A brown juice was prepared in the same manner as in (3) of Laboratory-test Example 7.

(4) Preparation of plant-protecting compositions

A plant-protecting composition, referred to as the composition J hereinbelow, was prepared by mixing 2 parts by weight of the chitosan hydrolyzate D prepared in (1) above, 1 part by weight of a fermented vinegar containing 10% by weight of acetic acid and 2 parts by weight of pure water.

Another plant-protecting composition, referred to as the composition K hereinbelow, was prepared by mixing 2 parts by weight of the chitosan hydrolyzate D prepared in (1) above, 2 parts by weight of the acetic acid-containing solution prepared in (2) above and 1 part by weight of pure water.

A further plant-protecting composition, referred to as the composition L hereinbelow, was prepared by mixing 2 parts by weight of the chitosan hydrolyzate D prepared in (1) above, 1 part by weight of a fermented vinegar containing 10% by weight of acetic acid, 1 part by weight of pure water and 1 part by weight of the brown juice prepared in (3) above.

A still further plant-protecting composition, referred to as the composition M hereinbelow, was prepared by mixing 2 parts by weight of the chitosan hydrolyzate D prepared in (1) above, 2 parts by weight of the acetic acid-containing solution prepared in (2) above and 1 part by weight of the brown juice prepared in (3) above.

(5) Tests of plant disease control and chemical injuries
i) Plant disease tested: bacterial grain rot of rice
ii) Strain of rice: "nihonbare"
iii) Plant growth: medium seedlings transplanted by machine on Jun. 23, 1989; earing on Aug. 22, 1989
iv) Testing zone: 6 m² per zone
v) Application of the plant-protecting composition: working solutions were prepared by diluting the compositions J, K, L and M prepared in (4) above each by 10 times, 50 times, 100 times and 200 times and applicated twice on Aug. 22 and 25, 1989 in a volume of 150 liters per 10 ares by using a shoulder-carried full-automatic spraying machine.
vi) Inspection: once on Sep. 12, 1989
vii) Results As is shown in Table 14, appearance of bacterial grain rot of rice could be controlled by applicating the solutions prepared by 10 times to 200 times dilution of the compositions J, K, L and M twice after earing. Chemical injuries were found in the zones where a high preventive effect was obtained by applicating a high concentration solution. The chemical injuries were less significant in the zones where the composition K, which was prepared by mixing the chitosan hydrolyzate D and the acetic acid-containing solution, was used. No chemical injuries were found in the zones where application was performed of the solutions prepared from the composition L or M with admixture of the brown juice, in this regard of chemical injuries, no difference was noted between the composition L, prepared by using the fermented vinegar as the acetic acid source, and the composition M, prepared by using the acetic acid-containing solution prepared in (2) above as the acetic acid source.

TABLE 14

|  | Dilution, times | % Diseased ears | Disease severity | Preventive value | Chemical injuries |
| --- | --- | --- | --- | --- | --- |
| Control | — | 91.0 | 52.2 |  |  |
| Plant-protecting | 10 | 42.6 | 15.5 | 70.3 | + |

TABLE 14-continued

|  | Dilution, times | % Diseased ears | Disease severity | Preventive value | Chemical injuries |
| --- | --- | --- | --- | --- | --- |
| composition (J) | 50 | 46.2 | 21.0 | 59.8 | ± |
|  | 100 | 67.4 | 31.0 | 40.7 | — |
|  | 200 | 78.6 | 41.1 | 21.3 | — |
| Plant-protecting composition (K) | 10 | 43.0 | 15.8 | 69.7 | + |
|  | 50 | 47.2 | 21.6 | 58.7 | ± |
|  | 100 | 64.9 | 29.4 | 43.6 | — |
|  | 200 | 76.3 | 39.3 | 24.8 | — |
| Plant-protecting composition (L) | 10 | 40.8 | 14.4 | 72.5 | ± |
|  | 50 | 49.1 | 22.0 | 57.9 | — |
|  | 100 | 68.3 | 30.9 | 40.9 | — |
|  | 200 | 75.8 | 39.1 | 25.1 | — |
| Plant-protecting composition (M) | 10 | 39.8 | 13.7 | 73.8 | ± |
|  | 50 | 44.9 | 20.8 | 60.2 | — |
|  | 100 | 62.8 | 28.3 | 45.8 | — |
|  | 200 | 77.9 | 40.4 | 22.6 | — |

Chemical injuries:
—; no chemical injuries found
±; chemical injuries found but no problem in practical application
%, diseased ears = (number of diseased ears)/(number of inspected ears) × 100
disease severity = (3A + 2B + 1C)/3 (number of inspected ears) × 100 in which A: number of ears with more than ⅔ of diseased husk grains; B: number of ears with ⅓ — ⅔ diseased husk grains; and C: number of ears with less than ⅓ of diseased husk grains Field-test

EXAMPLE 8

(1) Preparation of a chitosan hydrolyzate
A hydrolysis product of chitosan, referred to as the chitosan hydrolyzate C. hereinbelow, was prepared in the same manner as in (1) of Laboratory-test Example 5.

(2) Preparation of an acetic acid-containing solution
An acetic acid-containing solution was prepared in the same manner as in (2) of Laboratory-test Example 5.

(3) Preparation of a brown juice
A brown juice was prepared in the same manner as in (3) of Laboratory-test Example 7.

(4) Preparation of plant-protecting compositions
A plant-protecting composition, referred to as the composition N hereinbelow, was prepared by mixing 2 parts by weight of the chitosan hydrolyzate C prepared in (1) above, 1.5 parts by weight of a fermented vinegar containing 10% by weight of acetic acid and 1.6 parts by weight of pure water.

Another plant-protecting composition, referred to as the composition O hereinbelow, was prepared by mixing 2 parts by weight of the chitosan hydrolyzate C prepared in (1) above, 3 parts by weight of the acetic acid-containing solution prepared in (2) above and 0.1 part by weight of pure water.

A further plant-protecting composition, referred to as the composition P hereinbelow, was prepared by mixing 2 parts by weight of the chitosan hydrolyzate C prepared in (1) above, 3 parts by weight of the acetic acid-containing solution prepared in (2) above and 0.1 part by weight of the brown juice prepared in (3) above.

(5) Tests of plant disease control and chemical injuries
i) Plant disease tested: scab of peach
ii) Strain of the fruit tree: "hakuho", 18-years old trees
iii) Testing zone: one tree per zone
iv) Application of the plant-protecting composition: working solutions were prepared by diluting the compositions N, O and P prepared in (4) above each by 20 times, 50 times, 100 times and 250 times and applicated 5 times in every 10 days during the period beginning with May 2 and ending with Jun. 14, 1989 in a volume of 5 liters per tree by using a shoulder-carried full-automatic spraying machine.
v) Inspection: once on Jul. 14, 1989
vi) Results As is shown in Table 15, appearance of scab of peach could be controlled by using the solutions prepared by 20 times to 250 times dilution of the compositions N, O and P although some chemical injuries were found with the compositions N and O. The results support the practical usefulness of the composition P with admixture of the brown juice in the prevention of the scab of peach.

TABLE 15

|  | Dilution, times | Number of fruits inspected | % Diseased fruits (%) | Disease severity | Preventive value | Chemical injuries |
|---|---|---|---|---|---|---|
| Control | — | 50 | 89.3 | 44.4 |  |  |
| Plant-protecting composition (N) | 20 | 80 | 24.3 | 16.1 | 63.8 | + |
|  | 50 | 80 | 34.8 | 19.1 | 56.9 | ± |
|  | 100 | 80 | 50.7 | 23.0 | 48.2 | — |
|  | 200 | 80 | 69.8 | 29.9 | 32.7 | — |
| Plant-protecting composition (O) | 20 | 80 | 24.0 | 14.1 | 68.3 | + |
|  | 50 | 80 | 32.8 | 17.4 | 60.9 | ± |
|  | 100 | 80 | 52.4 | 23.6 | 46.8 | — |
|  | 200 | 80 | 68.3 | 29.9 | 32.7 | — |
| Plant-protecting composition (P) | 20 | 80 | 25.2 | 15.9 | 64.3 | ± |
|  | 50 | 80 | 33.0 | 17.9 | 59.7 | — |
|  | 100 | 80 | 51.8 | 23.3 | 47.6 | — |
|  | 200 | 80 | 71.3 | 31.4 | 29.4 | — |

Chemical injuries:
—; no chemical injuries found
±; chemical injuries found but no problem in practical application
+; practical detrimental chemical injuries found
% diseased fruits = (number of diseased fruits)/(number of inspected fruits) × 100
disease severity = Σ(number of diseased fruits in each degree × factor)/(number of inspected fruits) × 100
factor 1: 1–5 lesion per fruit
factor 2: 6–20 lesion per fruit
factor 3: 21–50 lesion per fruit
factor 4: 51 or more lesion per fruit

What is claimed is:

1. A method for protecting vegetables against bacterial soft rot which comprises applying to the vegetables or to a field thereof an effective protecting amount of a plant-protecting composition consisting essentially of (a) 0.0036 to 0.029% by weight of chitosan hydrolyzate having an average molecular weight from 10,000 to 50,000 and (b) 0.002 to 0.018% by weight of acetic acid, the chitosan hydrolyzate and the acetic acid being in a weight ratio of 1:0.25 to 1:4.

2. The method as claimed in claim 1, wherein the composition further contains (c) a deproteinized juice of alfalfa leaves.

3. The method as claimed in claim 2, wherein the deproteinized juice of alfalfa leaves is in an amount from 2 to 20% by weight based on the amount of the composition.

4. A method for protecting turfgrass against spring deadspot, which comprises applying to the turfgrass an effective protecting amount of a plant-protecting composition consisting essentially of (a) 0.0097 to 0.29% by weight of chitosan hydrolyzate having an average molecular weight from 10,000 to 50,000 and (b) 0.0061 to 0.18% by weight of acetic acid, the chitosan hydrolyzate and the acetic acid being in a weight ratio of 1:0.43 to 1:2.3.

5. The method as claimed in claim 4, wherein the composition further contains (c) a deproteinized juice of alfalfa leaves.

6. The method as claimed in claim 5, wherein the deproteinized juice of alfalfa leaves is in an amount from 2 to 20% by weight based on the amount of the composition.

7. A method for protecting rice against bacterial grain rot which comprises applying to the rice or to a field thereof an effective protecting amount of a plant-protecting composition consisting essentially of (a) 0.01 to 0.2% by weight of chitosan hydrolyzate having an average molecular weight from 10,000 to 50,000 and (b) 0.01 to 0.2% by weight of acetic acid, the chitosan hydrolyzate and the acetic acid being in a weight ratio of 1:0.43 to 1:2.3.

8. The method as claimed in claim 7, wherein the composition further contains (c) a deproteinized juice of alfalfa leaves.

9. The method as claimed in claim 8, wherein the deproteinized juice of alfalfa leaves is in an amount from 2 to 20% by weight based on the amount of the composition.

10. A method for protecting a fruit tree against scab which comprises applying to the fruit tree or to a field thereof an effective protecting amount of a plant-protecting composition consisting essentially of (a) 0.0098 to 0.098% by weight of chitosan hydrolyzate having an average molecular weight from 10,000 to 50,000 and (b) 0.0145 to 0.145% by weight of acetic acid, the chitosan hydrolyzate and the acetic acid being in a weight ratio of 1:0.25 to 1:4.

11. The method as claimed in claim 10, wherein the composition further contains (c) a deproteinized juice of alfalfa leaves.

12. The method as claimed in claim 11, wherein the deproteinized juice of alfalfa leaves is in an amount from 2 to 20% by weight based on the amount of the composition.

13. A method for protecting turfgrass against Rhizoctonia large patch or Rhizoctonia brown patch which comprises applying to the turfgrass an effective protecting amount of a plant-protecting composition consisting essentially of (a) 0.0097 to 0.29% by weight of chitosan hydrolyzate having an average molecular weight from 10,000 to 50,000 and (b) 0.0061 to 0.18% by weight of acetic acid, the chitosan hydrolyzate and the acetic acid being in a weight ratio of 1:0.43 to 1:2.3.

14. The method as claimed in claim 13, wherein the composition further contains (c) a deproteinized juice of alfalfa leaves.

15. The method as claimed in claim 14, wherein the deproteinized juice of alfalfa leaves is in amount from 2 to 20% by weight based on the amount of the composition.

16. A method for protecting turfgrass against Helminthosporium leaf blight which comprises applying to the turfgrass an effective protecting amount of a plant-protecting composition consisting essentially of (a) 0.0097 to 0.29% by weight of chitosan hydrolyzate having an average molecular weight from 10,000 to 50,000 and (b) 0.0061 to 0.18% by weight of acetic acid, the chitosan hydrolyzate and the acetic acid being in a weight ratio of 1:0.25 to 1:4.

17. The method a claimed in claim 16, wherein the composition further contains (c) a deproteinized juice of alfalfa leaves.

18. The method as claimed in claim 17, wherein the deproteinized juice of alfalfa leaves is in amount from 2 to 20% by weight based on the amount of the composition.

* * * * *

UNITED STATES PATENT AND TRADEMARK OFFICE
CERTIFICATE OF CORRECTION

PATENT NO. : 5,374,627
DATED : December 20, 1994
INVENTOR(S) : ITO et al

It is certified that error appears in the above-indentified patent and that said Letters Patent is hereby corrected as shown below:

Title page, [56] References Cited, under FOREIGN PATENT DOCUMENTS, rewrite "1128775" as --1-128775--; insert the following:

Signed and Sealed this

Twenty-eighth Day of January, 1997

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,374,627
DATED : December 20, 1994
INVENTOR(S) : ITO et al

It is certified that error appears in the above-indentified patent and that said Letters Patent is hereby corrected as shown below:

On the Title page, item [56] References Cited, please insert the following:

```
--3-58905      3/1991      Japan
  53-41219    11/1978      Japan
  1-291799    11/1989      Japan
  62-198604    9/1987      Japan--.
```

Signed and Sealed this

Second Day of September, 1997

Attest:

BRUCE LEHMAN

Attesting Officer

Commissioner of Patents and Trademarks